United States Patent
Vaidya et al.

(10) Patent No.: US 6,379,599 B1
(45) Date of Patent: Apr. 30, 2002

(54) PROCESS FOR THE PREPARATION OF MOLECULARLY IMPRINTED POLYMERS USEFUL FOR SEPARATION OF ENZYMES

(75) Inventors: Alankar Arun Vaidya; Bhalchandra Shripad Lele; Mohan Gopalkrishna Kulkarni; Raghunath Anant Mashelkar, all of Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/481,650

(22) Filed: Jan. 10, 2000

(51) Int. Cl.$^7$ .............................. C08J 5/00; C08F 2/44
(52) U.S. Cl. ...................... 264/220; 264/108; 264/221; 264/225; 264/226; 264/227; 264/330; 264/331.11; 435/7.1; 435/41; 435/128; 435/134; 435/177; 435/182; 435/814; 526/199; 526/200; 526/201; 526/215; 526/243; 526/317.1; 526/318.43
(58) Field of Search .................................. 264/108, 220, 264/227, 330, 331.11; 435/7.1, 41, 128, 134, 177, 182, 814; 526/199, 200, 201, 215, 243, 317.1, 318.43

(56) References Cited

U.S. PATENT DOCUMENTS

| 5,310,648 A | * | 5/1994 | Arnold et al. | 435/5 |
| 5,587,273 A | * | 12/1996 | Yan et al. | 430/269 |
| 5,858,296 A | * | 1/1999 | Domb | 264/330 |
| 5,959,050 A | * | 9/1999 | Mosbach et al. | 526/201 |

* cited by examiner

Primary Examiner—Herbert J. Lilling
(74) Attorney, Agent, or Firm—Powell, Goldstein, Frazer & Murphy, LLP

(57) ABSTRACT

The invention relates to a process for the preparation of molecularly imprinted polymers useful for separation of enzymes, which comprises the steps of reacting a complex of enzyme and affinity monomer, a comonomer and a crosslinker, with a polymerization initiator and a polymerization accelerator at ambient temperature and pressure for a period ranging between 2 to 24 hrs, thereby obtaining a crosslinked polymer, crushing the cross linked polymer obtained to fine particles, adding a solvent and extracting imprinted enzyme from the polymer, obtaining the molecularly imprinted polymer, contacting the imprinted polymer with aqueous solution containing imprinted enzyme or a mixture of imprinted enzyme and other enzymes and isolating the enzyme-adsorbed polymer.

18 Claims, No Drawings

PROCESS FOR THE PREPARATION OF MOLECULARLY IMPRINTED POLYMERS USEFUL FOR SEPARATION OF ENZYMES

FIELD

This invention relates to a process for the preparation of molecularly imprinted polymers useful for separation of enzymes. Molecularly imprinted polymers prepared by the process of the invention exhibit selective binding of imprinted enzyme, which is useful in separating the imprinted enzyme from aqueous solution of the imprinted enzyme or a mixture containing imprinted enzyme and other enzymes.

BACKGROUND

Purifications and isolations of biological macromolecules like proteins and enzymes are critical multi-stop processes as they result in very low yields and thus high cost. As a better alternative to the conventional processes, researchers have developed various techniques for purification of enzymes which can broadly be classified as follows.
1. Affinity chromatography (Y. Li, G. Kunyu, C. Lubai, Z. Hanfa, Z. Yunkui Sepu, 14:415 (1996), T. Makriyannis, Y. D. Clonis, Biotech. Bioengg. 53.49 (1997)).
2. Affinity precipitation (C. Senstad, B. Mattiasson, Biotech. Bioengg. 33:216 (1989), M. Schneider, C. Guillot, B. Lamy, Ann. N.Y. Acad. Sci. 369:257 (1981)).
3. Affinity crossflow ultrafiltration (K. Sigmundsson, H. Filippusson, Polymer int. 41:355(1996), T. B. Choe, P. Masse, A. Verdier, Biotech. Lett. 8:163 (1986)).
4. Affinity partitioning (G. Takerkart, E. Segard, M. Monsigny, FEBS Lett. 42:218 (1972), B. A. Andrews, D. M. Head, P. Dunthorne, J. A. Asenjo, Biotech. Tech. 4:49 (1990)).
5. Immobilized metal affinity chromatography (G. Ehteshami, J. Porath, R. Guzmnan, G. Ehteshami, J. Mol. Recognit. 9:733 (1996), A. L. Blomkalns, M. R. Gomez, Prep. Biochem. Biotechnol. 27:219 (1997)).
6. Molecularly imprinted immobilized metal affinity chromatography (F. H. Arnold, P. Dhal, D. Shnek, S. Plunkett, U.S. Pat. No. 5,310,648 (1994)).

These techniques exploit either the binding interaction between active site of an enzyme and its inhibitor i.e. affinity monomer or between surface histidine, tyrosine, cysteine groups of enzymes with metal ions immobilized on a support. But these techniques also suffer from one or the other disadvantages as follows.

Affinity chromatography uses a column containing an inhibitor or a dye or an antibody for a given enzyme for its separation from a mixture of enzymes. The solution of enzymes is poured over the affinity column to retain the desired enzyme on column for subsequent isolation. This technique is efficient only for small capacity columns. With the scale up of columns, the problems of sample pretreatment and plugging of packed column become severe.

The affinity precipitation technique needs a complex to be formed between a macro-ligand and a protein both containing multiple binding sites. When such a complex is formed, it precipitates. Thus, this technique is restricted mainly for multimeric proteins. Beside such macro-ligands are often costly. Therefore, certain synthetic inhibitors or dyes are linked to stimuli responsive polymer which can be precipitated by pH or temperature stimuli after it forms a complex with the enzyme. In this case along with the desired enzyme, a substantial amount of other enzymes bind to the polymer by means of nonspecific adsorption.

In case of affinity crossflow ultrafiltration, a solution of enzymes is filtered through a membrane containing affinity group under pressure. This technique is suitable in cases where the difference between molecular weights of two enzymes is high. Also, with increase in filtration time, denaturation of enzyme as well as clogging of the membrane takes place due to pressure applied.

Affinity partitioning of two-phase aqueous systems is widely used technique as compared to those mentioned above. In this technique concentrated aqueous solution of poly(ethylene glycol) (PEG) with or without linking affinity group is mixed with enzyme solution containing moderate a high salt concentration. The two phases are mixed well and allowed to separate. The enzyme gets predominantly partitioned in one phase, which subsequently can be isolated. Disadvantages of this technique are nonspecific extraction of other proteinaceous molecules along with desired enzyme and also poor interactions between enzyme and affinity group due to high ionic strength.

Immobilized metal affinity chromatography is a technique in which columns of polymeric support containing chelated metal ions are used. These metal ions form coordination complex with histidine, tyrosine, crysteine etc present on the surface of the enzyme. Although this technique has advantages like high column capacity, ease in enzyme elution etc. it is not very selective in discriminating between two closely related (with respect to their amino acid sequences) enzymes.

Molecular imprinting of matrices containing metal chelates is a recently developed technique, which increases the selectivity (F. H. Arnold, P. Dhal, D. Shnek, S. Plunkett, U.S. Pat. No. 5,310,648 (1994)). In this technique, complex of monomer containing chelated metal ion and enzyme is polymerized with crosslinker in order to imprint the polymer with enzyme. Although this technique exhibits a substantial selectivity, it is not as selective as that of biological antibodies or active site inhibitors of enzymes.

Synthetic inhibitors are molecules which exhibit affinity to the active site of a given enzyme. This interaction is very specific for a given pair of enzyme and inhibitor and such inhibitors bind very strongly to a given enzyme.

Molecular imprinting is a simple technique which allows synthesis of polymers capable of recognizing specific molecules. These polymers are stable and can withstand harsh conditions such as temperature and pH etc (G. Wolff, Molecular interactions in Bioseparations Ed. by T. T. Nao., Plenum press, N.Y. (1993)). Thus, these polymers are finding wide range of applications. A polymer containing monomer based on enzyme inhibitor i.e. affinity monomer which is also imprinted for corresponding enzyme is expected to exhibit a high selectivity as well as high capacity for binding a specific enzyme. This synergistic affinity-imprinting effect will not be available in the above mentioned techniques. Such affinity-imprinted polymers have not been reported so far.

OBJECTS

The object of the present invention is to provide a process for the preparation of molecularly imprinted polymers comprising affinity monomers imprinted for various enzymes, affinity imprinting technique, useful for achieving high selectivity as well as high capacity for separation of enzymes.

DETAILED DESCRIPTION

Accordingly the present invention provides a process for the preparation of molecularly imprinted polymers useful for separation of enzymes which comprises the steps of:

(i) reacting the complex of enzyme and affinity monomer, a comonomer and a crosslinker, with a polymerization initiator and a polymerization accelerator at ambient temperature and pressure for a period ranging between 2 to 24 hrs. thereby obtaining a crosslinked polymer, (ii) crushing the cross linked polymer obtained to fine particles, (iii) adding a solvent and extracting imprinted enzyme from the polymer, (iv) obtaining the molecularly imprinted polymer, and (v) contacting the imprinted polymer with aqueous solution containing imprinted enzyme or a mixture of imprinted enzyme and other enzymes and isolating the enzyme-adsorbed polymer.

In one embodiment, the enzymes are selected from the group of enzymes and proteins comprising trypsin, chymotrypsin, lysozyme, and ovalbumin (nonenzyme nutritional protein).

In another embodiment, the complexing affinity monomers are selected from the group comprising acryloyl derivatives of inhibitors for respective enzymes such as N-acryloyl para amino benzamidine, N-acryloyl 4-phenyl butyl amine, acryloyl N-acetyl glucosamine, and N-oleoylacrylamide respectively, and the enzyme-affinity monomer complex may be prepared by contacting aqueous solutions of enzyme and the respective affinity monomer.

In another embodiment, affinity monomers, N-acryloyl para amino benzamidine, N-acryloyl 4-phenyl butyl amine, acryloyl N-acetyl glucosamine and N-oleylecrylamide may be prepared by the reaction of acryloyl chloride with para amino benzamidine, 4-phenyl butyl amine, N-acetyl glucosamine and acrylamide respectively.

In yet another embodiment, the ratio of enzyme to affinity monomer may be in the range of 1:1 to 1:10, preferably 1:1 (w/w).

In a further another embodiment, the comonomer may be selected from compounds such as acrylamide, methacrylamide, N-isopropylacrylamide, N-isopropylmethacrylamide, acrylic acid, methacrylic acid and the like.

In another embodiment, the amount of comonomer in the polymerization mixture may be in the range of 5 to 80%, more particularly 45 to 55% by weight of the total feed (i.e. enzyme-affinity monomer complex=comonomer-crosslinker, hereinafter).

In still another embodiment, crosslinker may be selected from compounds such as methylene bisacrylamide, N, N diacryloyl 1,2 diaminoethane, N, N dimethacryloyl 1,2 diaminoethane, N, N diacryloyl 1,6 diaminohexane, ethylene glycol dimethacrylate and the like.

In still another embodiment, the amount of crosslinker may be between 10% to 90%, more particularly 30 to 50% by weight of the total feed.

In yet another embodiment, the polymerization initiator used may be selected from compounds such as ammonium persulfate, ceric ammonium sulfate, potassium persulfate, azobisisobutyronitrile and the like.

In yet another embodiment, the amount of polymerization initiator may be 0.1% to 1% by weight of the total feed.

In still another embodiment, the polymerization accelerator may be selected from compounds such as ethylene diamine, N, N, N, N tetramethylene ethylenediamine and the like.

In still another embodiment, the amount of polymerization accelerator may be 1% to 4% by weight of the total feed.

In still another embodiment, the solvent used to extract the enzyme from the imprinted polymer may be selected from solvents which break the enzyme-inhibitor complex such as phenol, chloroform, glacial-acetic acid and the like.

In a feature of the present invention, the molecularly imprinted polymer is typically prepared under mild conditions as follows. An affinity monomer and its respective enzyme are dissolved in water and stirred for 15 to 30 minutes at room temperature to form the enzyme-affinity monomer complex. Then comonomer, crosslinker and polymerization initiator are added to the solution containing enzyme-affinity monomer complex and the solution is purged with nitrogen for 10 minutes. Polymerization accelerator is then added and the solution is kept at 37° C. for 18 hours for polymerization. The crosslinked polymer so obtained is treated with acetone to remove water and crushed to small particles. Template enzyme is extracted from the particles by 3 to 4 alternative treatments of the solvent which breaks the complex between enzyme and the inhibitor. Polymer particles are then sieved and used for enzyme separations.

In another feature of the present invention, enzyme imprinted polymers are contacted with aqueous solution containing the respective enzyme or a mixture of enzymes and allowed to shake at room temperature for 1 hour. Polymer particles with bound enzyme are then filtered and isolated.

Although the present invention describes a process for the preparation of molecularly imprinted polymers useful for the separation of enzymes, namely trypsin, chymotrypsin, lysozyme and ovalbumin (nonenzyme nutritional protein), the scope of the present invention is not and should not be construed to limit only to such molecularly imprinted polymers for separation of trypsin, chymotrypsin, lysozyme and ovalbumin only but it may extend to such combinations of affinity monomers and their respective enzymes.

The ranges and limitations provided in the instant specification and claims are those which are believed to particularly point out and distinctly claim the present invention. It is however understood that other ranges and limitations which perform substantially the same function in the same or substantially the same manner to obtain the same or substantially the same results are intended to be within the scope of the instant invention as defined by the instant specification and claims.

EXAMPLE 1

Preparation of Trypsin Imprinted Polymer

In an air tight round bottom teflon tube 50 mg N-acryloyl para aminobenzamidine hydrochloride is dissolved in 3 ml. water containing a stoichiometric amount of sodium hydroxide so as to free guanidine group from its hydrochloride form. To this solution 50 mg trypsin is added; and the resulting solution is shaken gently on a shaker bath for 15 min; to form trypsin-N-acryloyl para aminobenzamidine complex. The comonomer acrylamide 400 mg; crosslinker methylene bis acrylamide 500 mg; and initiator ammonium per sulfate 10 mg are dissolved in 1 ml. Dimethyl formamide and this solution is added to above aqueous solution containing trypsin-N-acryloyl para aminobenzamidine complex. This is mixed well and nitrogen gas is passed through this solution for 10 min and 40 $\mu$l tetramethylene ethylenediamine is added. The teflon tube containing this solution is kept in a water bath at 37° C.; for 18 hrs. The gel so synthesized is treated with acetone to remove water. It is then crushed to fine particles.

Template trypsin is extracted from the particles by 3–4 alternative treatments of acetone and chloroform. The resulting trypsin imprinted polymer is then dried in vacuum oven at 50° C. for 12 hrs. Dried polymer particles are then sieved through standard test sieves and particles in the size range of 250–500 µ are used for enzyme separation.

EXAMPLE 2

Preparation of Chymotrypsin Imprinted Polymer

In an air tight round bottom teflon tube 50 mg N-acryloyl 4 phenyl butylamine is dissolved in 3 ml. dimethyl formamide/water mixture (20:80). To this solution 50 mg chymotrypsin is added; and the resulting solution is shaken gently on a shaker bath for 15 min; to form chymotrypsin-N-acryloyl 4 phenyl butyl amine complex.

The comonomer acrylamide 400 mg; crosslinker methylene bis acrylamide 500 mg; and initiator ammonium per sulfate 10 mg are dissolved in 1 ml. Dimethyl formamide and this solution is added to above aqueous solution containing chymotrypsin-N-acryloyl 4 phenyl butylamine complex. This is mixed well and nitrogen gas is passed through this solution for 10 min. and 40 µl tetramethylene ethylenediamine is added. The teflon tube containing this solution is kept in a water bath at 37° C.; for 18 hrs. The gel so synthesized is treated with acetone to remove water. It is then crushed to fine particles.

Template chymotrypsin is extracted from the particles by 3–4 alternative treatments of acetone and chloroform. The resulting chymotrypsin imprinted polymer is then dried in vacuum oven at 50° C. for 12 hrs. Dried polymer particles are then sieved through standard test sieves and particles in the size range of 250–500 µ are used for enzyme separation.

EXAMPLE 3

Preparation of Lysozyme Imprinted Polymer

In an air tight round bottom teflon tube 50 mg acryloyl N-acetyl glucosamine is dissolved in 3 ml water. To this solution 20 mg lysozyme is added; and the resulting solution is shaken gently on a shaker bath for 15 min; to form lysozyme-acryloyl N-acetyl glucosamine complex. The comonomer acrylamide 400 mg; crosslinker methylene bis acrylamide 500 mg; and initiator ammonium persulfate 10 mg are dissolved in 1 ml. dimethyl formamide and this solution is added to above aqueous solution containing lysozyme-acryloyl N-acetyl glucosamine complex. This is mixed well and nitrogen gas is passed through this solution for 10 min and 40 µl tetramethylene ethylenediamine is added. The teflon tube containing this solution is kept in a water bath at 37° C.; for 18 hrs. The gel so synthesized is treated with acetone to remove water. It is then crushed to fine particles.

Template lysozyme is extracted from the particles by 3–4 treatments of glacial acetic acid. The resulting lysozyme imprinted polymer is then dried in vacuum oven at 50° C. for 12 hrs. Dried polymer particles are then sieved through standard test sieves and particles in the size range of 250–500 µ are used for enzyme separation.

EXAMPLE 4

Preparation of Ovalbumin Imprinted Polymer

In an air tight round bottom teflon tube 50 mg N-oleoyl acrylamide is dissolved in 3 ml. dimethyl formamide/water mixture (20:80). To this solution 50 mg ovalbumin is added; and the resulting solution is shaken gently on a shaker bath for 15 min; to form ovalbumin-N-oleoyl acrylamide complex. The comonomer acrylamide 400 mg; crosslinker methylene bis acrylamide 500 mg; and initiator ammonium per sulfate 10 mg are dissolved in 1 ml dimethyl formamide and this solution is added to above aqueous solution containing ovalbumin-N-oleoyl acrylamide complex. This is mixed well and nitrogen gas is passed through this solution for 10 min and 40 µl tetramethylene ethylenediamine is added. The teflon tube containing this solution is kept in a water bath 37° C. for 18 hours. The gel so synthesized is treated with acetone to remove water. It is then crushed to fine particles.

Template albumin is extracted from the particles by 3–4 treatments of phenol-chloroform. The resulting ovalbumin imprinted polymer is then dried in vacuum oven at 50° C. for 12 hrs. Dried polymer particles are then sieved through standard test sieves and particles in the size range of 250–500 µ are used for enzyme separation.

In all the above-mentioned examples, formation of enzyme-affinity monomer complex was confirmed by the active site titration of respective complexes.

EXAMPLE 5

The example describes the process for selective binding of trypsin by trypsin-imprinted polymer from trypsin and chymotrypsin mixture.

In a 50 ml capacity conical flask; 250 mg trypsin imprinted polymer is suspended in 25 ml 10 mM $Ca^{+2}$ aqueous solution containing trypsin and chymotrypsin with equal initial activities. The flask is allowed to shake at 50 rpm speed at room temperature on a rotary shaker for 1 hr. The swollen polymer particles are then filtered and in the filtrate the activities of trypsin and chymotrypsin are determined by using following standard substrates. For trypsin DL-benzoyl-arginyl-para nitroanilide, and for chymotrypsin L-benzoyl-tyrosyl-para nitroanilide are used.

Uptake of trypsin by the polymer was determined by subtracting the activity of trypsin in the filtrate from the initial activity of trypsin in the solution. It was found that activity wise 40 percent trypsin and only 2.6 percent chymotrypsin was adsorbed by trypsin imprinted polymer.

EXAMPLE 6

This example describes the process for selective binding of chymotrypsin by chymotrypsin imprinted polymer from chymotrypsin and trypsin mixture.

In a 50 ml. capacity conical flask; 250 mg chymotrypsin imprinted polymer is suspended in 25 ml 10 mM $Ca^{+2}$ aqueous solution containing trypsin and chymotrypsin with equal initial activities. The flask is allowed to shake at 50 rpm speed at room temperature on a rotary shaker for 1 hr. The swollen polymer particles are then filtered and in the filtrate the activities of trypsin and chymotrypsin are determined by using following standard substrates. For trypsin DL-benzoyl-arginyl-para nitroanilide, and for chymotrypsin L-benzoyl-tryroyl-para nitroanilide are used.

Uptake of chymotrypsin by the polymer was determined by subtracting the activity of chymotrypsin in the filtrate from the initial activity of chymotrypsin in the solution. It was found that activity wise 52 percent chymotrypsin and only 4 percent trypsin was adsorbed by chymotrypsin imprinted polymer.

EXAMPLE 7

This example describes the process for binding of lyszyme by lysozyme imprinted polymer from lysozyme solution.

In a 50 ml. capacity conical flask; 250 mg lysozyme imprinted polymer is suspended in 25 ml 0.06 M phosphate buffer; pH=6,8 containing 2.5 mg lysozyme. The flask is allowed to shake at 50 rpm speed at room temperature on a rotary shaker for 1 hr. The swollen polymer particles are then filtered and in the filtrate the activity of lysozyme is determined by using *Micrococus hyzodeikticus*, a standard substrate for lysozyme.

Uptake of lysozyme by the polymer was determined by subtracting the activity of lysozyme in the filtrate from the initial activity of lysozyme in the solution. It was found that activity wise 60% lysozyme was adsorbed by lysozyme imprinted polymer.

EXAMPLE 8

This example describes the process for binding of ovaltumin by ovalbumin imprinted polymer from ovalbumin solution.

In a 50 ml. capacity conical flask; 250 mg ovalbumin imprinted polymer is suspended in 25 ml water containing 2.5 mg ovalbumin (determined by absorbance at 280 nm). The flask is allowed to shake at 50 rpm speed at room temperature on a rotary shaker for 1 hr. The swollen polymer particles are then filtered and in the filtrate the ovaalbumin in terms of protein (determined from standard graph at 280 nm) is determined by using pure ovalbumin as a standard. Uptake of ovalbumin by the polymer was determined by subtracting the protein present in the filtrate from the initial protein added in the solution. It was found that protein wise 45% percent ovalbumin was adsorbed by ovalbumin imprinted polymer.

The advantages of the present invention are as follows:
1. The process of the present invention, unlike the other conventional processes, exhibits a very high selectivity as well as very high capacity for separating the imprinted enzyme either from a mixture of enzymes or from their aqueous solutions.
2. The process of the present invention is applicable in general for separating various other enzymes by preparing affinity imprinted polymers as mentioned herein above using appropriate complexing affinity monomer and the respective enzyme.
3. The process of the present invention is convenient and the polymers synthesized by following the present process are resistant to denaturation by the action of organic solvent, high temperature and pressure.

What is claimed is:
1. A process for the preparation of a molecularly imprinted polymer useful for separation of enzymes, which comprises the steps of
   (i) reacting a complex of enzyme and an affinity monomer that specifically recognizes the enzyme, a comonomer, and a crosslinker, with a polymerization initiator and a polymerization accelerator at ambient temperature and pressure for 2 to 24 hrs., thereby obtaining a crosslinked polymer,
   (ii) crushing the crosslinked polymer obtained to fine particles,
   (iii) adding a solvent and extracting the enzyme from the polymer, and
   (iv) obtaining the molecularly imprinted polymer.

2. A process as claimed in claim 1 wherein the enzyme is selected from the group consisting of trypsin, chymotrypsin, lysozyme and ovalbumin.

3. A process as claimed in claim 1 wherein the complexing affinity monomer is an acryloyl derivative of an enzyme inhibitor selected from the group consisting of N-acryloyl-para-aminobenzamidine, N-acryloyl-4-phenylbutylamine, acryloyl-N-acetylglucosamine, and N-oleoylacrylamide.

4. A process as claimed in claim 1 wherein the enzyme-affinity monomer complex is prepared by contacting aqueous solutions of enzyme and the respective affinity monomer.

5. A process as claimed in claim 1 wherein the affinity monomer is prepared by reacting acryloyl chloride with para-aminobenzamidine, 4-phenylbutylamine, or N-acetylglucosamine, and acrylamide.

6. A process as claimed in claim 1 wherein the ratio of enzyme to affinity monomer is 1:1 to 1:10 (w/w).

7. A process as claimed in claim 1 wherein the comonomer is selected from the group consisting of acrylamide, methacrylamide, N-isopropylacrylamide, N-isopropylmethacrylamide, acrylic acid, and methacrylic acid.

8. A process as claimed in claim 1 wherein the amount of comonomer in the polymerization mixture is 5 to 80% by weight of the total feed.

9. A process as claimed in claim 1 wherein the crosslinker is selected from the group consisting of methylene bisacrylamide, N,N-diacryloyl-1,2-diaminoethane, N,N-dimethacryloyl-1,2-diaminoethane, N,N-diacryloyl-1,6-diaminohexane, and ethylene glycol dimethacrylate.

10. A process as claimed in claim 1 wherein the amount of crosslinker is from about 10% to about 90% by weight of the total feed.

11. A process as claimed in claim 1 wherein the polymerization initiator is selected from the group consisting of ammonium persulfate, ceric ammonium sulfate, potassium persulfate, and azobis(isobutyro)nitrile.

12. A process as claimed in claim 1 wherein the amount of polymerization initiator is from about 0.1% to about 1% by weight of the total feed.

13. A process as claimed in claim 1 wherein the polymerization accelerator is ethylenediamine or N,N,N,N-tetramethylethylenediamine.

14. A process as claimed in claim 1 wherein the amount of polymerization accelerator is 1% to 4% by weight of the total feed.

15. A process as claimed in claim 1 wherein the solvent used to extract the enzyme from the imprinted polymer is selected from the group consisting of phenol, chloroform, and glacial acetic acid.

16. A process as claimed in claim 1 wherein the ratio of enzyme to affinity monomer is 1:1 (w/w).

17. A process as claimed in claim 1 wherein the amount of comonomer in the polymerization mixture is 45 to 55% by weight of the total feed.

18. A process as claimed in claim 1 wherein the amount of crosslinker is from about 30% to about 50% by weight of the total feed.

* * * * *